United States Patent
Teitelbaum et al.

(10) Patent No.: US 11,123,526 B2
(45) Date of Patent: Sep. 21, 2021

(54) CRANK MECHANISM FOR BALLOON INFLATION DEVICE

(71) Applicant: Merit Medical Systems, Inc., South Jordan, UT (US)

(72) Inventors: Jason Scott Teitelbaum, West Nyack, NY (US); Pratik Amarish Shukla, New York, NY (US); Tejas Pankaj Patel, Piscataway, NJ (US); Aakash Paresh Madhu, Monmouth Junction, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 133 days.

(21) Appl. No.: 15/669,033

(22) Filed: Aug. 4, 2017

(65) Prior Publication Data

US 2018/0036520 A1    Feb. 8, 2018

Related U.S. Application Data

(60) Provisional application No. 62/371,483, filed on Aug. 5, 2016.

(51) Int. Cl.
*A61M 25/10*    (2013.01)
*A61M 29/02*    (2006.01)

(52) U.S. Cl.
CPC .... *A61M 25/10182* (2013.11); *A61M 25/104* (2013.01); *A61M 29/02* (2013.01)

(58) Field of Classification Search
CPC .......... A61M 25/10182; A61M 25/104; A61M 25/10181; A61M 25/1018; A61M 25/10184; A61M 29/02; G05G 1/085
See application file for complete search history.

(56) References Cited

U.S. PATENT DOCUMENTS

| | | | |
|---|---|---|---|
| 2,747,574 A | 5/1956 | De Lorenzo | |
| 4,161,891 A | 7/1979 | Bossert | |
| 4,651,738 A | 3/1987 | Demer et al. | |
| 4,655,749 A | 4/1987 | Fischione | |
| 4,723,938 A | 2/1988 | Goodin et al. | |
| 4,758,223 A | 7/1988 | Rydell | |
| 4,781,192 A * | 11/1988 | Demer .............. | A61M 25/1018 606/195 |
| 4,919,121 A | 4/1990 | Rydell et al. | |

(Continued)

FOREIGN PATENT DOCUMENTS

| | | |
|---|---|---|
| EP | 0213765 | 3/1987 |
| EP | 0396353 | 3/1995 |

(Continued)

OTHER PUBLICATIONS

International Search Report and Written Opinion dated Jun. 27, 2018 for PTC/US2018/019378.

(Continued)

*Primary Examiner* — Jocelin C Tanner

(74) *Attorney, Agent, or Firm* — Stoel Rives LLP

(57) ABSTRACT

Devices used to pressurize, depressurize, or otherwise displace fluid are disclosed. The devices may be configured to displace fluid in order to inflate or deflate a medical device, such as a balloon. The devices may further include a crank member for providing a mechanical advantage when pressurizing or otherwise displacing fluid.

8 Claims, 6 Drawing Sheets

(56) References Cited

U.S. PATENT DOCUMENTS

| | | | |
|---|---|---|---|
| 4,940,459 A | 7/1990 | Noce | |
| 5,047,015 A | 9/1991 | Foote et al. | |
| 5,057,078 A | 10/1991 | Foote et al. | |
| 5,150,853 A * | 9/1992 | Bernard | A01K 89/006 |
| | | | 242/283 |
| 5,163,904 A | 11/1992 | Lampropoulos et al. | |
| 5,209,732 A | 5/1993 | Lampropoulos et al. | |
| 5,213,115 A | 5/1993 | Zytkovicz et al. | |
| 5,306,248 A | 4/1994 | Barrington | |
| 5,472,424 A | 12/1995 | Lampropoulos et al. | |
| 5,685,848 A | 11/1997 | Robinson et al. | |
| 5,741,229 A | 4/1998 | Robinson et al. | |
| 5,904,342 A * | 5/1999 | Laarman | B60S 9/08 |
| | | | 16/406 |
| 6,106,496 A | 8/2000 | Arnissolle | |
| 6,471,671 B1 | 10/2002 | Urick et al. | |
| 6,834,670 B2 | 12/2004 | Rosine et al. | |
| 7,041,084 B2 | 5/2006 | Fojtik | |
| 8,372,030 B2 | 2/2013 | Dixon et al. | |
| 8,545,442 B2 | 10/2013 | Lampropoulos et al. | |
| 8,758,294 B2 | 7/2014 | Kim et al. | |
| 2004/0084084 A1 | 5/2004 | Rosine et al. | |
| 2005/0234493 A1* | 10/2005 | Carr | A61B 17/7098 |
| | | | 606/181 |
| 2008/0077075 A1 | 3/2008 | Moreira et al. | |
| 2009/0151484 A1 | 6/2009 | Mullen et al. | |
| 2010/0211007 A1 | 8/2010 | Lesch, Jr. et al. | |
| 2010/0298836 A1* | 11/2010 | Jordan | A61B 17/7098 |
| | | | 606/94 |
| 2013/0123693 A1 | 5/2013 | Lampropoulos et al. | |
| 2013/0165899 A1 | 6/2013 | Haueter et al. | |
| 2013/0331780 A1 | 12/2013 | Lampropoulos et al. | |
| 2014/0074141 A1 | 3/2014 | Johnson et al. | |
| 2014/0081205 A1 | 3/2014 | Kanner et al. | |
| 2014/0088499 A1* | 3/2014 | Lampropoulos | A61M 25/10182 |
| | | | 604/97.02 |
| 2014/0168958 A1 | 6/2014 | Unger et al. | |
| 2015/0051543 A1 | 2/2015 | Chadwick et al. | |
| 2016/0199091 A1 | 7/2016 | Pigott | |
| 2018/0036520 A1 | 2/2018 | Teitelbaum et al. | |
| 2018/0243540 A1 | 8/2018 | Sykes et al. | |
| 2018/0264509 A1 | 9/2018 | Pauser et al. | |
| 2019/0240418 A1 | 8/2019 | Takahashi et al. | |
| 2020/0230379 A1 | 7/2020 | Simmons et al. | |
| 2020/0282191 A1* | 9/2020 | McArthur | A61M 25/10184 |

FOREIGN PATENT DOCUMENTS

| | | |
|---|---|---|
| JP | 61009561 | 12/1986 |
| WO | 2009128393 | 10/2009 |
| WO | 2012094403 | 7/2012 |
| WO | 2015023923 | 2/2015 |
| WO | 2015134568 | 9/2015 |

OTHER PUBLICATIONS

International Search Report and Written Opinion dated Nov. 15, 2017 for PCT/US2017/045456.
Office Action dated Feb. 3, 2020 for U.S. Appl. No. 15/903,372.
Office Action dated Jul. 20, 2020 for U.S. Appl. No. 15/903,372.
European Search Report dated Mar. 5, 2020 for EP17837742.0.
International Search Report and Written Opinion dated May 20, 2020 for PCT/US2020/013921.
International Search Report and Written Opinion dated Jun. 30, 2020 for PCT/US2020/020996.
European Search Report dated Nov. 23, 2020 for EP18756701.1.

* cited by examiner

CRANK MECHANISM FOR BALLOON INFLATION DEVICE

RELATED APPLICATION

This application claims priority to U.S. Provisional Application No. 62/371,483 filed Aug. 5, 2016, titled CRANK MECHANISM FOR BALLOON INFLATION DEVICE, the entire contents of all of which are hereby incorporated by reference.

TECHNICAL FIELD

The present disclosure relates generally to devices used to pressurize, depressurize, or otherwise displace fluid, particularly in medical devices. More specifically, the present disclosure relates to high-pressure devices used to pressurize, depressurize, or otherwise displace fluid along a line in order to inflate or deflate a medical device, such as a balloon.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
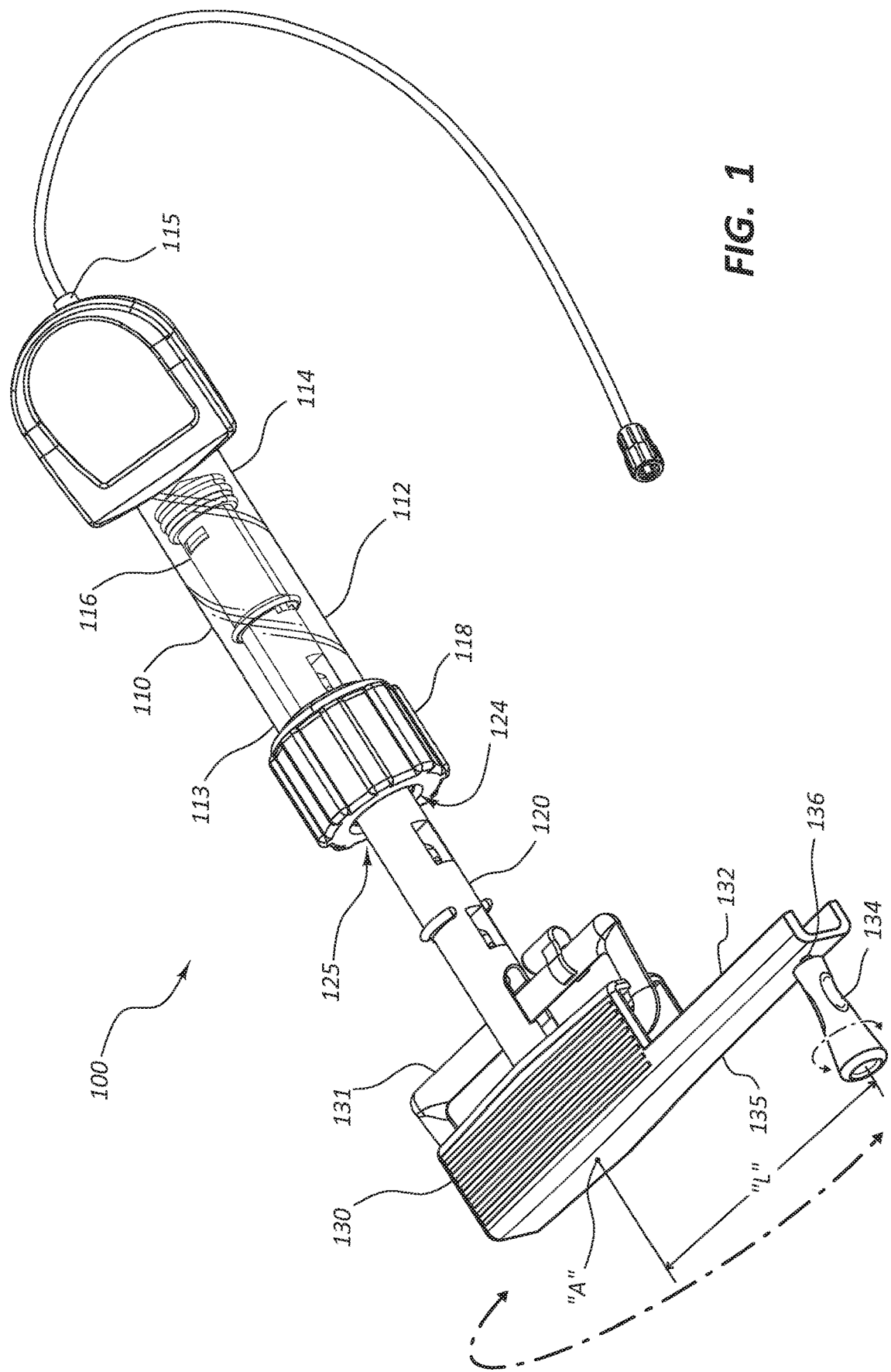
FIG. 1 is a perspective view of an inflation device with an integrated crank member.

Angioplasty is a common medical procedure in which a collapsed balloon is inserted endovascularly into a narrowed vessel segment and subsequently inflated to apply outward radial force on the wall of the stenotic lesion in an attempt to restore a vessel caliber to its original dimensions. Medical advancement has allowed for medical balloons to be utilized in many different anatomic regions for repair of pathologically disrupted organs, including but not limited to arterial or venous structures, nasal sinuses, biliary ducts, and the gastrointestinal system. These procedures typically utilize man powered plastic disposable inflation devices. Inflation devices may rely on a practitioner performing a twisting mechanism of their wrist with repetitive pronation and supination of the forearm to advance a plunger within a syringe containing fluid (e.g. contrast and/or saline). As fluid is advanced from the barrel into a balloon through connection tubing, hydraulic pressure increases resulting in expansion of the balloon according to Pascal's principle. Often, the twisting motion must be performed by the user several hundred times during a single procedure, resulting in pain to the user and potentially causing work-related musculoskeletal injury. Inflation devices may not be designed with optimal ergonomic consideration. Using medical inflation devices can be extremely difficult and painful for practitioners due to overuse of hand and forearm muscles.

Accordingly, the present disclosure provides a balloon inflation device to allow the user to incrementally increase pressure with fine detail without causing such stress and overtaxing of the user's arm musculature during manipulation of the inflation device. In some embodiments, this can be achieved by manipulating a crank that may extend from the handle of an inflation device for purposes of advancing fluid into a balloon catheter. The crank allows the practitioner to maintain their wrist and forearm in a neutral position, by performing circular motion of the hand about the axis of the elbow, which is much more comfortable and sustainable to the practitioner, as opposed to repeated supination/pronation of the forearm and wrist. The crank allows the threadlike method of piston advancement and preserves the ability of inflation device to operate in freely reciprocating mode.

In some embodiments, an inflation device is provided containing a crank that is visually intuitive such that the practitioner with minimal skill in the art of angioplasty will understand to advance the piston utilizing the thread like motion. This can be beneficial when the balloon catheter is located within delicate anatomic regions of the patient's body.

The inflation device may include the syringe which utilizes threads to advance or retract the plunger by rotating the plunger handle relative to the body of the syringe such that the threads cause longitudinal displacement of the plunger relative to the body. In some instances, the inflation syringe may further include retractable threads, enabling the practitioner to disengage the threads and displace the plunger by simply pushing or pulling the plunger.

The inflation syringe may comprise a coupling member configured to constrain movement of the plunger within the syringe body. The coupling member may comprise threads configured to engage with the retractable threads. Certain inflation devices include a mechanism in the handle of the device which allows the practitioner to disengage the threads through manipulating the mechanism. For example, in some instances the handle of such a device may include the "trigger" portion which may be configured to retract threads positioned on the plunger that were engaged with the coupling member when the trigger is actuated, thereby disengaging the threads from the coupling member.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Fluid" is used in its broadest sense, to refer to any fluid, including both liquids and gases as well as solutions, compounds, suspensions, etc., which generally behave as fluids.

FIGS. 1-5 illustrate different views of several inflation devices and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2:
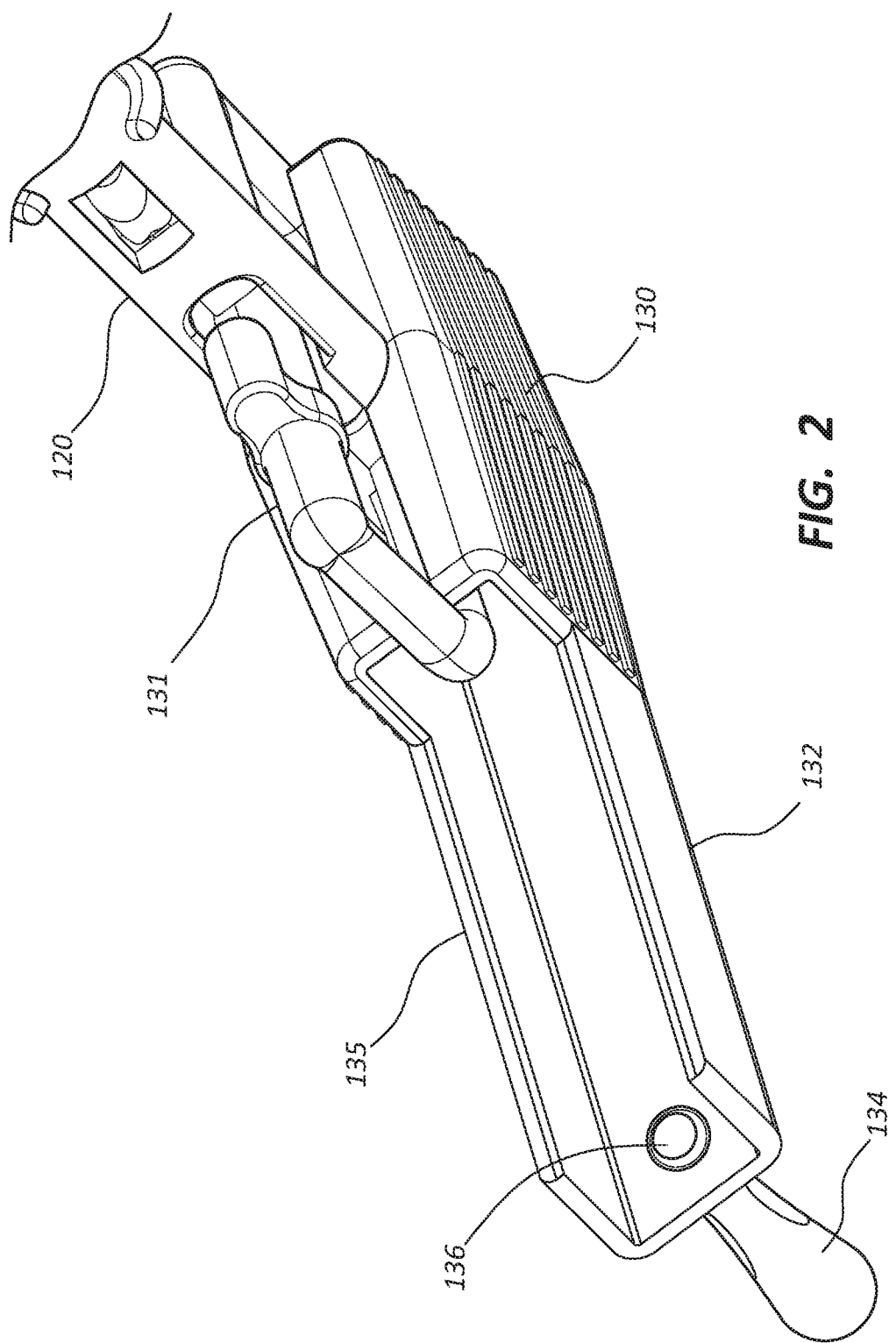
FIG. 2 is a partially cut-away perspective view of the integrated handle and crank member of the inflation device of FIG. 1.

FIGS. 1-2 depict one embodiment of an inflation device 100. In the illustrated embodiment, the inflation device 100 is partially comprised of a syringe 110. The inflation device 100 includes three broad groups of components; each group may have numerous subcomponents and parts. The three broad component groups are: a body component such as syringe body 112, a pressurization component such as plunger 120, and a handle 130.

The syringe body 112 may be formed of a generally cylindrical hollow tube configured to receive the plunger 120. The syringe body 112 may include an inlet/outlet port 115 located adjacent the distal end 114 of the syringe body 112. In some embodiments, a coupling member 118 may be coupled to the syringe body 112 adjacent the proximal end 113 of the syringe body 112. The coupling member 118 may include a center aperture configured to allow the plunger 120 to pass through the coupling member 118 into the syringe body 112. Further, the coupling member 118 may include coupling member threads configured to selectively couple the coupling member 118 to the plunger 120. For example, the coupling member 118 may comprise a polymeric nut at the proximal end 113 of the syringe body 112.

The plunger 120 may be configured to be longitudinally displaceable within the syringe body 112. The plunger 120 may be comprised of a plunger shaft coupled to a plunger seal at the distal end of the plunger shaft. The plunger shaft may also be coupled to the handle 130 at the proximal end of the plunger shaft, with the plunger shaft spanning the distance between the plunger seal and the handle 130.

The handle 130 broadly refers to the group of components coupled to the proximal end of the plunger 120, some of which may be configured to be graspable by a user. In certain embodiments, the handle 130 may be configured such that the user may manipulate the position of the plunger 120 by manipulating the handle 130. Further, in some embodiments, the handle 130 may be an actuator mechanism configured to manipulate components of the inflation device 100.

Any and every component disclosed in connection with any of the exemplary handle configurations herein may be optional. That is, though the handle 130 broadly refers to the components coupled to the proximal end of the plunger shaft which may be configured to be graspable by a user, use of the term "handle" is not meant to indicate that every disclosed handle component is always present. Rather, the term is used broadly, referring to the collection of components, but not specifically referring to or requiring the inclusion of any particular component. Likewise, other broad groupings of components disclosed herein, such as the syringe 110 or syringe body 112 and the plunger 120, may also refer to collections of individual subcomponents. Use of these terms should also be considered non-limiting, as each subcomponent may or may not be present in every embodiment.

As shown in FIGS. 1-2, a fluid reservoir 116 may be defined by the space enclosed by the inside walls of the syringe body 112 between the plunger seal and the distal end 114 of the syringe body 112. Accordingly, movement of the plunger seal with respect to the syringe body 112 will alter the size and volume of the fluid reservoir 116.

In some embodiments, the syringe 110 may include a coupling member 118, fixedly coupled to the proximal end 113 of the syringe body 112. The coupling member 118 may utilize threads or other coupling mechanisms to fixedly couple the coupling member 118 to corresponding threads on the syringe body 112. Additionally, the coupling member 118 may engage external plunger threads 125 configured to couple the plunger 120 to the coupling member 118. The plunger 120 may thus be translated longitudinally with respect to the syringe body 112 by rotating the plunger 120 such that the interaction of the coupling member threads and the plunger threads 125 results in the longitudinal translation of the plunger 120. Such rotating motion may be achieved when a practitioner grasps the handle 130 and rotates it clockwise to extend the plunger 120 distally or counterclockwise to retract the plunger 120 proximally.

Thus, when the plunger threads 125 and the coupling member threads are engaged, movement of the plunger 120 is constrained with respect to the syringe body 112, though the plunger 120 is not necessarily fixed with respect to the syringe body 112. For example, the plunger 120 may be rotatable, but not directly translatable, when the threads are engaged.

The plunger threads 125 may be configured such that they may be retracted within the plunger shaft. In some embodiments, the plunger threads 125 do not extend 360 degrees around the axis of the plunger shaft. For example, the plunger threads 125 may be formed on a thread rail 124 on the plunger shaft. The thread rail 124 may be retracted from the threads of the coupling member 118 by actuating a mechanism such as a trigger 131.

The retractable threads may allow a practitioner to displace the plunger shaft relative to the syringe body 112 either through rotation of the plunger shaft (and the subsequent interaction of threads), or by retracting the plunger threads 125 and displacing the plunger shaft by applying opposing forces on the plunger shaft and the syringe body 112. (The forces, of course, may move the plunger shaft distally or proximally with respect to the syringe body 112.) Both methods of displacement may be utilized during the course of a single therapy.

In some instances, a practitioner may desire to quickly displace the plunger shaft, for instance, while priming the inflation device or while priming or deflating an attached medical device such as a balloon. Quick displacement of the plunger shaft may be accomplished by retracting the plunger threads 125 and sliding the plunger shaft relative to the syringe body 112. For example, a practitioner may quickly fill the fluid reservoir 116 with fluid by disengaging the plunger threads 125 and pulling the plunger shaft in a proximal direction with respect to the syringe body 112. Further, a practitioner may quickly force fluid into lines leading to a medical device or quickly expel unwanted air bubbles from the fluid reservoir 116 by retracting the plunger threads 125 and repositioning the plunger shaft.

In other instances, the practitioner may desire more precise control over the position of the plunger shaft (for example when displacing the plunger shaft in order to adjust the fluid pressure within the fluid reservoir 116) or it may simply be difficult to displace the plunger shaft due to high fluid pressure within the fluid reservoir 116. In these instances, the practitioner may opt to displace the plunger shaft by rotation of the plunger shaft.

When a practitioner rotates the handle 130, the plunger 120 is advanced distally or retracted proximally through the threaded engagement of the thread rail 124 and the coupling member 118. At high pressures, it can be difficult to rotate the handle 130 in order to increase the corresponding pressure in the balloon. The practitioner's hand may be gripping the handle 130 directly over the center rotation point "A". There is no mechanical advantage provided to reduce the force required to rotate the handle and advance the plunger 120. In the embodiment depicted in FIGS. 1-2, the handle 130 comprises a crank member 132 that extends radially outward, i.e., perpendicular from the longitudinal axis of the plunger 120, from the handle 130 in cantilevered fashion. The crank member 132 may comprise a shaft 135 and a knob 134. The shaft 135 may be configured as a polymeric, rectangular shaped rod or tube. In some embodiments, the shaft 135 may comprise an open channel, or alternatively comprise a solid piece of material. The shaft 135 may be integrally coupled to the handle 130 forming a unitary unit. The knob 134 may be disposed near a lateral end of the shaft 135 and oriented such that it is parallel to the longitudinal axis of the plunger 120. The knob 134 may be generally cylindrical in shape with grip enhancing features such as bi-concave recesses, bumps, dimples, texturing, etc. A spindle 136 may rotatably couple the knob 134 to the shaft 135 such that the practitioner does not need to release and re-grip the knob 134 as the crank member 132 is rotated. Other techniques known to the art may be used to rotatably couple the knob 134 to the shaft 135.

Rotation of the handle 130 using the crank member 132 uses the mechanical advantage of leverage to further advance the plunger 120 at high internal pressures while maintaining a reasonable input force delivered by the practitioner. The torque force produced to rotate the handle 130 about the center rotation point "A" is derived by the amount of force applied to the knob 134 multiplied by the length "L" of the crank member 132 from the center rotation point "A" to a central axis of the knob 134. Thus, a longer crank member 132 can provide a greater torque force while maintaining the same input force. The length "L" of the crank member 132 may range from three inches to six inches, including four inches to five inches. Additionally, utilization of the crank member 132 to rotate the handle 130 eliminates the supination/pronation motion of the wrist and forearm of the practitioner. During rotation of the crank member 132, the wrist and forearm remain in a neutral position as the elbow acts as a pivot point. Another factor determining an acceptable length of the crank member 132 may be the confined workspace the practitioner has available to work within while using the inflation device 100. In some instances, the crank member 132 should not be excessively long as it may interfere with equipment and other practitioners involved in a medical procedure as it is rotated.

The integrated crank member 132 allows a practitioner to use leverage in advancing the plunger 120 to achieve high pressures with the hand-held inflation device 100, while also permitting disengagement of the thread rail 124 from the coupling member 118 to rapidly move the plunger 120 longitudinally within the syringe body 112 without being restricted to only rotational movement of the handle 130 to advance or retract the plunger 120. For example, once high inflation pressures are achieved in the inflation device 100 using the crank member 132, deflation of the balloon can be achieved rapidly through actuating the trigger 131 to disengage the thread rail 124, thus not requiring a cranking motion to retract the plunger 120. The crank member 132 is configured to preserve the function of the trigger 131 such that the plunger 120 may be moved freely longitudinally within the syringe body.

Figure 3:
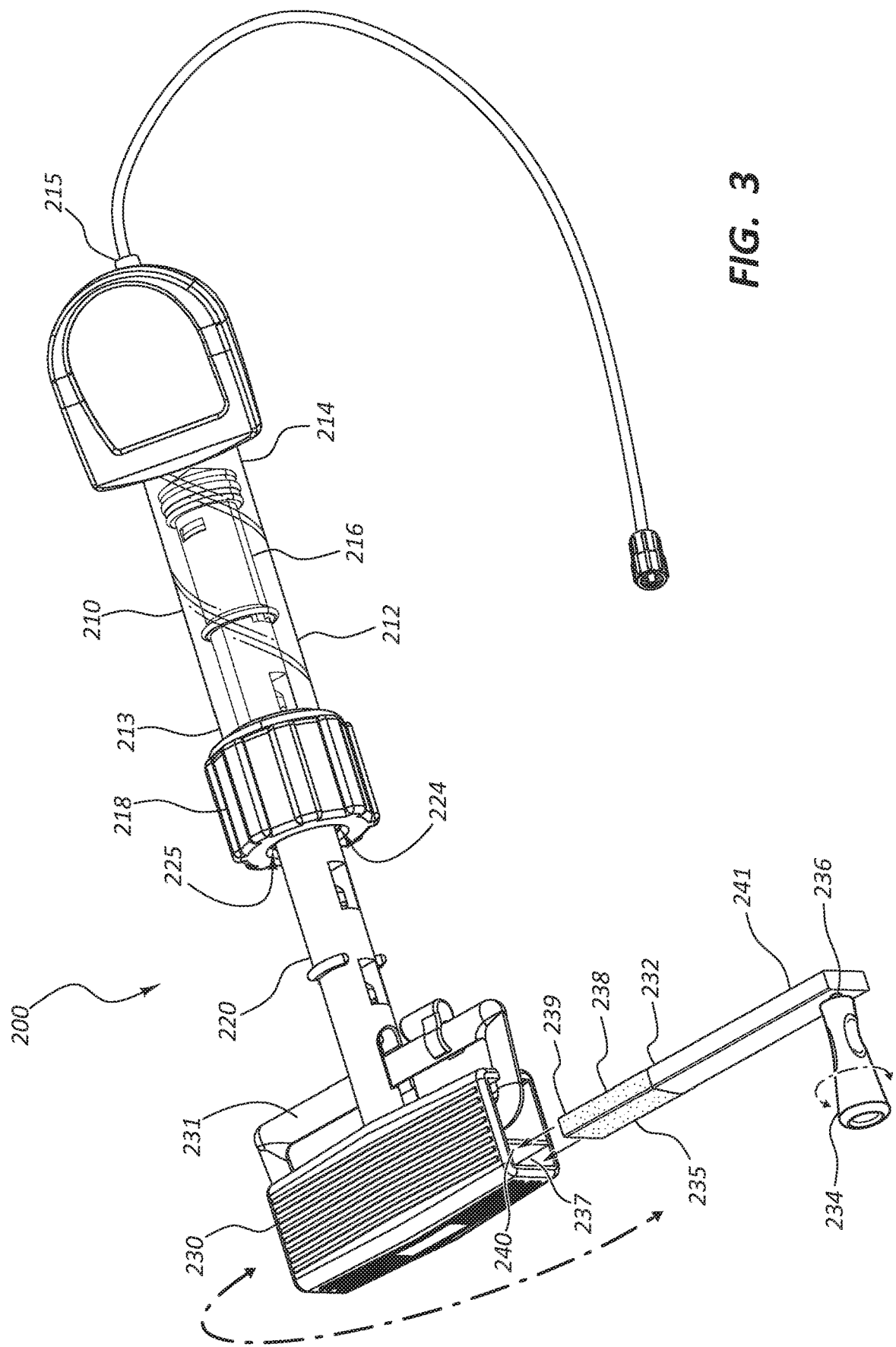
FIG. 3 is a perspective view of an inflation device with a releasable crank member prior to engagement with a handle.
Figure 4:
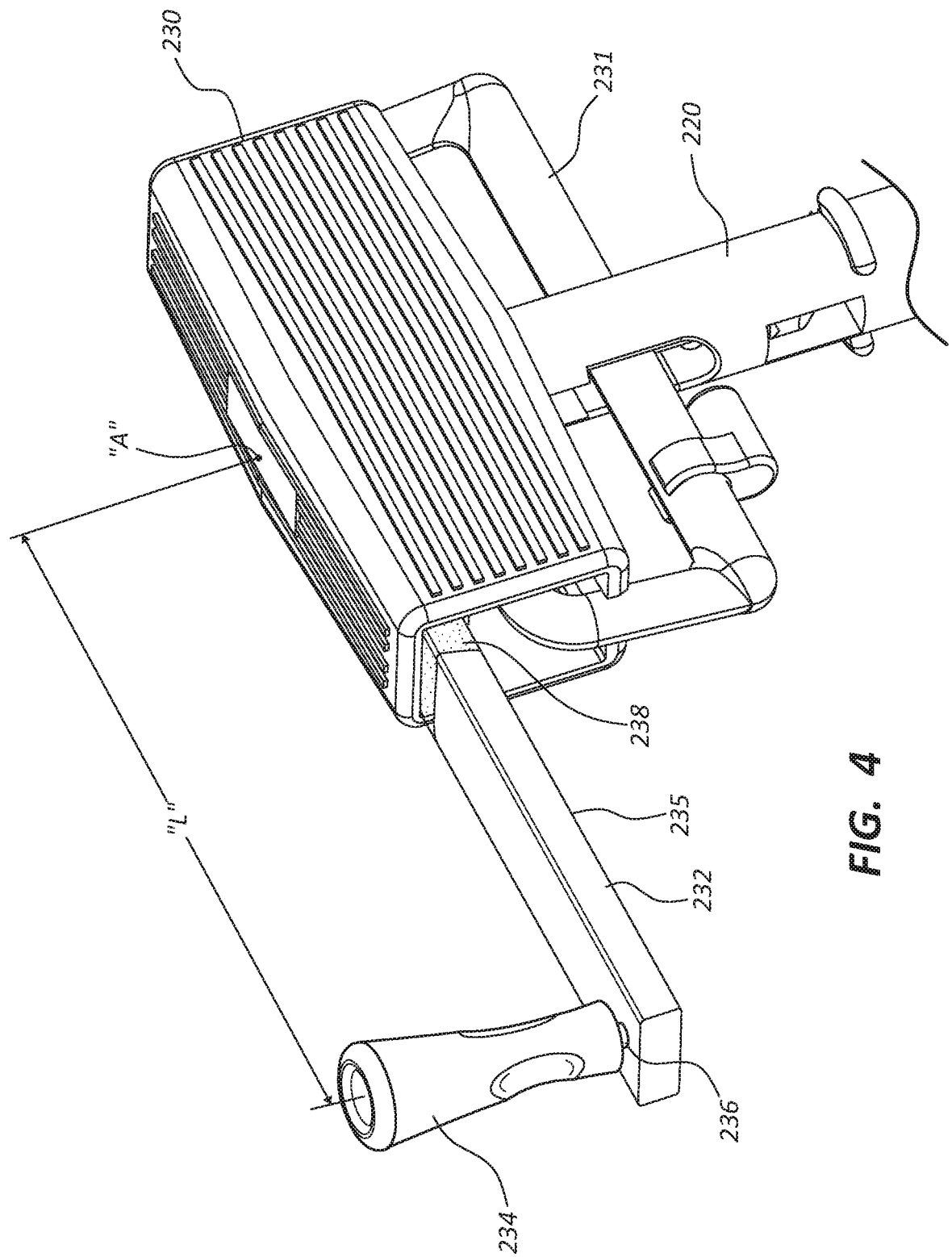
FIG. 4 is a perspective view of a portion of the inflation device of FIG. 3, with the releasable crank member partially disposed within the handle.

Referring now to FIGS. 3-4, an inflation device assembly 200 is shown with a detachable crank member 232. Similar to the embodiment of FIGS. 1-2, the inflation device assembly 200 includes a syringe 210 comprising a syringe body 212 having a proximal end 213 and distal end 214. A port 215 is disposed at the distal end 214 of the syringe body 212. The syringe body 212 further comprises a fluid reservoir 216. A coupling member 218 is disposed adjacent the proximal end 213 of the syringe body 212. The coupling member 218 is configured to engage a plunger 220 that extends within the syringe body 212. Engagement of the plunger 220 with the coupling member 218 may be accomplished by the releasably engagable thread rail 224 and plunger threads 225 as similarly described with the embodiment of FIGS. 1-2.

Adjacent the proximal end of the plunger 220 is a handle 230 and trigger mechanism 231 for selectively engaging or disengaging the thread rail 224 with the coupling member 218. The handle 230 is further configured to permit a practitioner to rotatably displace the plunger 220 with respect to the coupling member 218, which in turn advances and/or retracts the plunger 220 within the fluid reservoir 216. Furthermore, the handle 230 is configured to permit a practitioner to longitudinally displace the plunger 220 with respect to the coupling member 218, without the need of rotational movement when the thread rail 224 and plunger threads 225 are disengaged from the coupling member 218.

The crank member 232 is configured to releasably engage the handle 230. The crank member 232 extends laterally from the handle 230 (i.e., radially from the longitudinal axis of the plunger 220). In one embodiment a shaft 235 of the crank member 232 creates an interference fit with a channel or cavity 237 that is disposed within the handle 230. The cavity 237 is partially defined by a wall 240 that separates the cavity 237 from the trigger mechanism 231 such that the crank member 232, when inserted into the cavity 237, does not interfere with the function of the trigger mechanism 231. In one example, the shaft 235 includes a compliant portion 238 that is configured to engage the cavity 237 within the handle 230 to allow an interference fit. The compliant portion 238 may be configured with dimensions that are slightly larger than the dimensions of the cavity 237 such that the crank member is securely coupled to the handle 230 to create a mechanical advantage when rotating the handle 230. The compliant portion 238 may be formed from or coated with any suitable material such as rubber, silicone rubber, thermal plastic elastomer, etc. Alternatively, the compliant material may be coupled to the shaft 235 as a coating or a sleeve. Alternatively, the shaft may comprise detents, bumps, grooves or other features to engage with handle 230. The shaft 235 may be configured as a polymeric, rectangular shaped rod or tube. In some embodiments, the shaft 235 may comprise an open channel. The medial end 239 of the shaft 235 may be radiused or tapered to facilitate placement of the shaft 235 into the cavity 237.

In some embodiments, the crank member 232 may comprise a knob 234. The knob 234 may be configured for grasping by the practitioner's fingers. The knob 234 may be rotatably coupled to the shaft 235 near a lateral end 241 and oriented such that it is parallel to the longitudinal axis of the plunger 220. The knob 234 may be generally cylindrical in shape with grip enhancing features such as bi-concave recesses, bumps, dimples, texturing, etc. A spindle 236 may rotatably couple the knob 234 to the shaft 235 such that the knob 234 rotates as the crank member 232 is rotated allowing the practitioner to maintain a grip on the knob 234. Other techniques known in the art may be used to rotatably couple the knob 234 to the shaft 235.

Rotation of the handle 230 using the crank member 232 uses the mechanical advantage of leverage to further advance the plunger 220 at high internal pressures of the syringe 210 while maintaining a reasonable input force delivered by the practitioner. The torque force produced to rotate the handle 230 about a center rotation point "A" is derived by the amount of force applied to the knob 234 multiplied by the length "L" of the crank member 232 measured from the center rotation point "A" to a central axis of the knob 234. Thus, a longer crank member 232 can provide a greater torque force while maintaining the same input force. The length "L" of the crank member 232 can be adjusted by increasing or decreasing the depth of insertion the crank member 232 into the handle 230. For example, the torque force can be increased while maintaining a constant input force by increasing the length "L" of the crank member 232. This may be accomplished by decreasing the depth of insertion of the shaft 235 into the handle 230. Additionally, utilization of the crank member 232 to rotate the handle 230 eliminates the supination/pronation motion of the wrist and forearm of the practitioner. During rotation with the crank member 232, the wrist and forearm remain in a neutral position as the elbow acts as a pivot point. Another factor determining an acceptable length of the crank member 232 may be the confined workspace the practitioner has available to work within while using the inflation device 200. In some instances the crank member 232 should not be excessively long as it may interfere with equipment and other practitioners involved in a medical procedure as it is rotated. In some embodiments, length of the crank member 232 extending outside of the handle 230 may range from three inches to six inches, including four inches to five inches.

Figure 5:
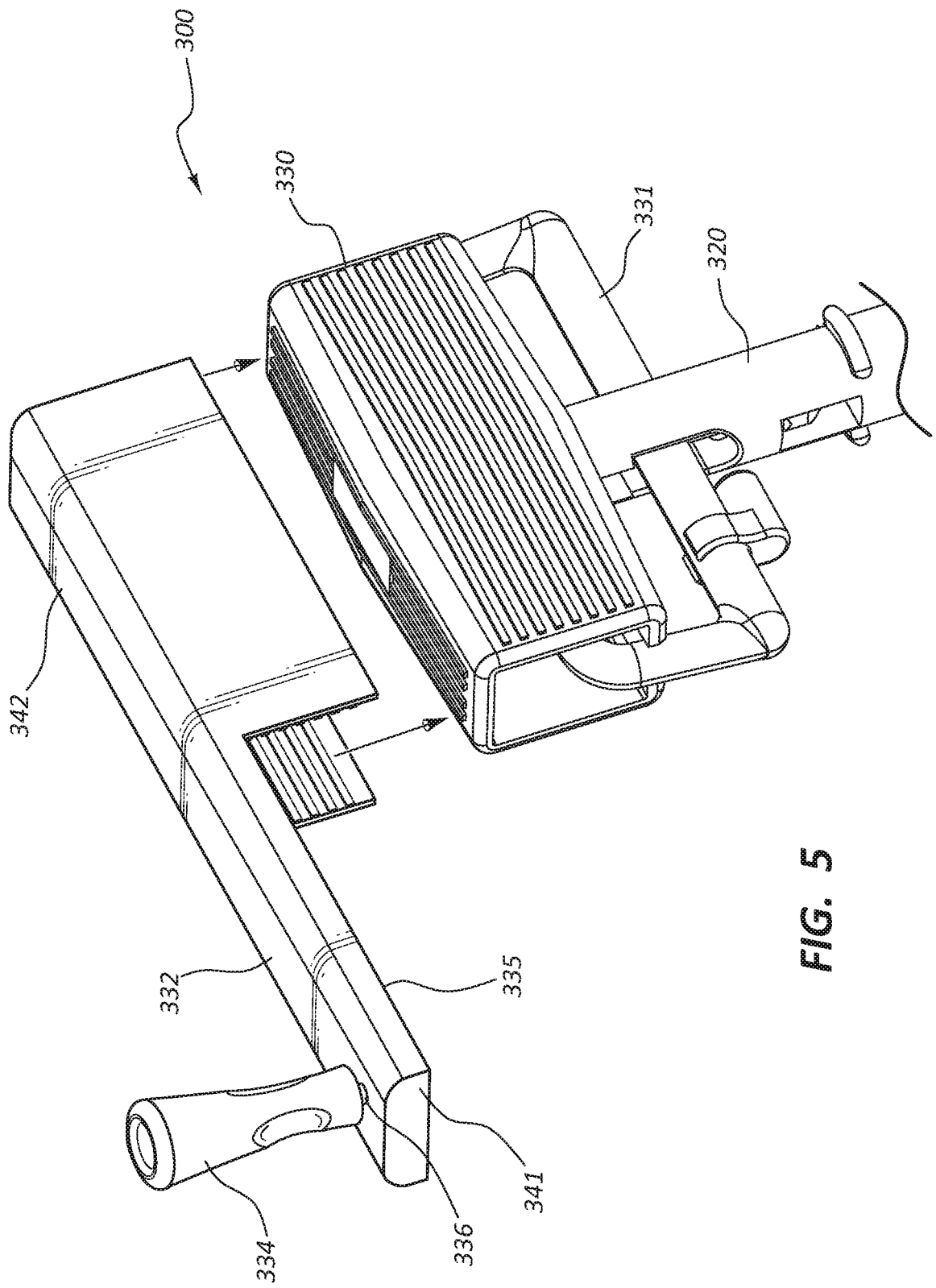
FIG. 5 is a perspective view of a portion of an inflation device with a releasable crank member configured to fit over a handle of the inflation device.

FIG. 5 shows a portion of an inflation device 300. Similarly, to the inflation devices 100 and 200 previously discussed, the inflation device 300 comprises a plunger 320, a handle 330, and a trigger 331. A crank member 332 is coupled to the handle 330. The crank member 332 comprises a handle cover 342, a shaft 335, and a knob 334. The handle cover 342 is configured to releasably fit over or snap on to the handle 330 such that the crank member 332 is coupled to the handle 330 to provide a mechanical advantage when the handle 330 is rotated. Alternatively, the crank member 332 may be coupled to the handle 330 using suction cups disposed within the handle cover 342. The shaft 335 extends from the handle cover 342 perpendicular to the longitudinal axis of the plunger 320. The shaft 335 may be formed as a rod, a tube or a channel. The knob 334 is rotatably coupled adjacent to the lateral end 341 of the shaft 335. A spindle 336 may couple the knob 334 to the shaft 335 such that the knob 334 rotates as the crank member 332 is rotated, allowing the practitioner to maintain a grip on the knob 334. The knob 334 may be generally cylindrical in shape with grip enhancing features such as bi-concave recesses, bumps, dimples, texturing, etc.

Figure 6:
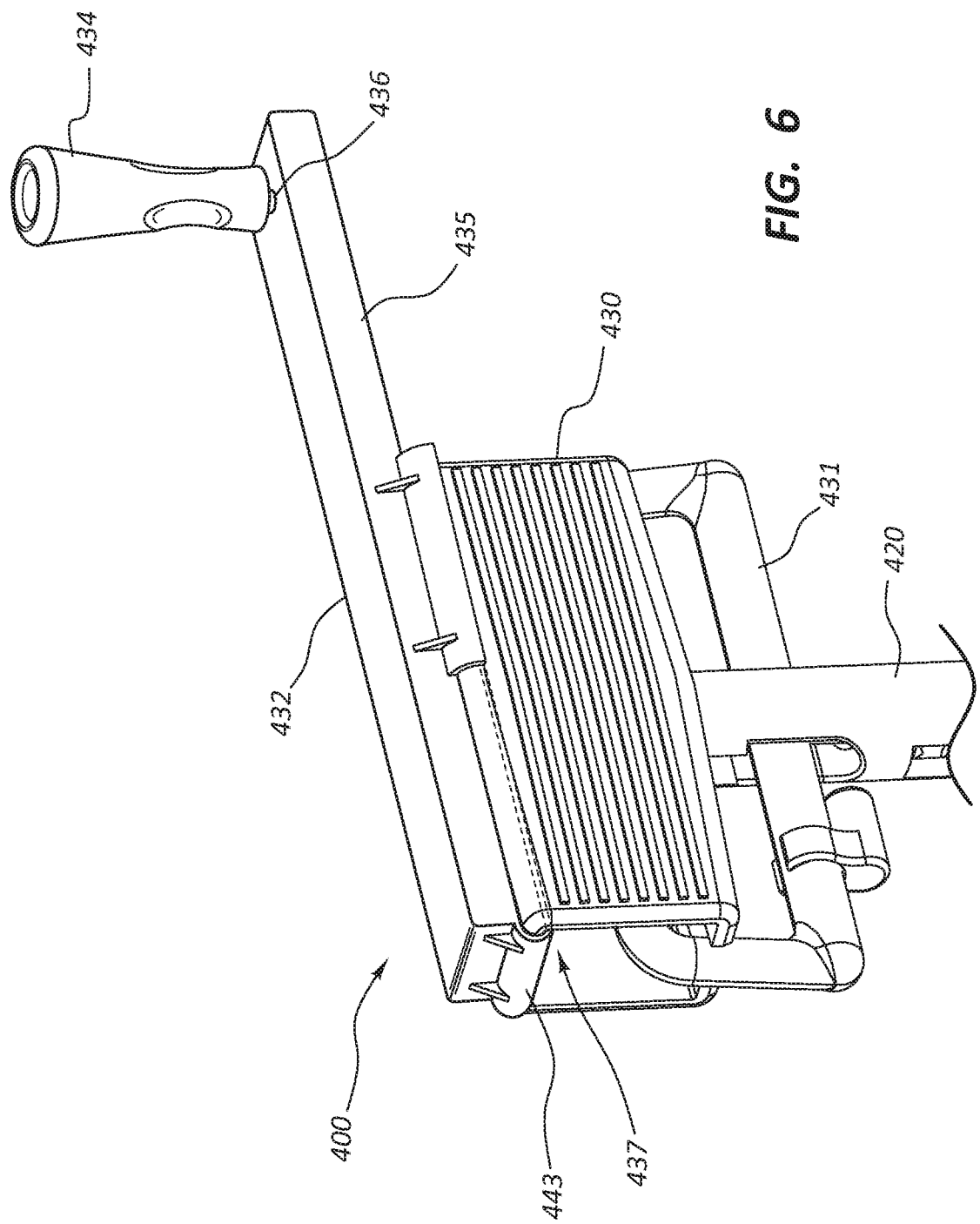
FIG. 6 is a perspective view of a portion of an inflation device with a releasable crank member configured to clip to or otherwise engage a handle of the inflation device.

FIG. 6 shows a portion of an inflation device 400. Similarly, to the inflation devices 100, 200, and 300 previously discussed, the inflation device 400 comprises a plunger 420, a handle 430, and a trigger 431. A crank member 432 is coupled to the handle 430. The crank member 432 comprises a shaft 435, a knob 434, and a U-shaped clip member 443. The clip member 443 is configured to be releasably disposed within a cavity 437 of the handle 430 such that the crank member 432 is coupled to the handle 430 to provide a mechanical advantage when the handle 430 is rotated. The length of the clip member 443 may extend the length of the cavity 437 such that the crank member 432 is more securely coupled to the handle 430. Alternatively, a free end of the clip member 443 may extend beyond the cavity 437 and comprise a feature to engage a receiving feature on the shaft 435 such that the shaft 435 and clip member 443 are coupled together around a portion of the handle 430. The shaft 435 extends from the handle 430 perpendicular to the longitudinal axis of the plunger 420. The shaft 435 may be formed as a rod, a tube or a channel. The knob 434 is rotatably coupled adjacent to the lateral end of the shaft 435. A spindle 436 may couple the knob 434 to the shaft 435 such that the knob 434 rotates as the crank member 432 is rotated, allowing the practitioner to maintain a grip on the knob 434. The knob 434 may be generally cylindrical in shape with grip enhancing features such as bi-concave recesses, bumps, dimples, texturing, etc.

A handle configured to provide a mechanical advantage when retracting a thread rail may be desirable for certain therapies that require large syringes or high pressure. Such therapies may also require a larger biasing force due to the size of the device or the pressure within the device. A handle providing a mechanical advantage may make devices configured for such therapies easier to use.

In use, the inflation devices and assemblies described above may be pressurized using any of the following steps or actions, each of which may be optional or interchanged. An inflation device is obtained which comprises a syringe body, a plunger within the syringe body, a handle coupled to the plunger (such as through a thread rail coupled to a coupling member) and a crank member coupled to the handle. Alternatively, the crank member may be releasably coupled to the handle by inserting the crank member into a cavity of the handle or fitting the crank member over the handle.

The plunger may be advanced by grasping the syringe body in one hand and rotating the crank member clockwise (as viewed from the proximal end) with the other hand. The crank member allows for a smooth, continuous motion utilizing an ergonomic movement as opposed to the repetitive spastic wrist pronation and supination required of the inflation device without a crank member. Additionally, the rotating knob allows the practitioner to maintain a grip of the crank member as opposed to the gripping and re-gripping of the handle that is required for the inflation device without the crank member. Before rotation of the crank member, the thread rail of the plunger may be disengaged from the syringe body (or coupling member). The plunger may be advanced through longitudinal movement of the handle to a first internal pressure. Then the thread rail may be re-engaged to the syringe body after reaching the first internal pressure. The plunger may be further advanced through rotational movement of the handle via the crank member to achieve a second pressure. After the therapy is complete or when desirous of depressurizing the syringe, the thread rail can be disengaged from the syringe body and retracted through longitudinal movement of the handle.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An inflation device assembly, comprising:
   a syringe body;
   a plunger configured for advancement and retraction within the syringe body; and
   a coupling member comprising coupling member threads configured to constrain movement of the plunger within the syringe body;
   a handle fixedly coupled to a proximal portion of the plunger such that the handle is configured to rotationally and axially displace the plunger, the handle comprising an elongate portion coupled to the plunger, the elongate portion extending in a direction perpendicular to a longitudinal axis of the plunger; and
   a crank member coupled to the elongate portion of the handle, wherein the crank member comprises a shaft extending from the handle in a direction perpendicular to the longitudinal axis of the plunger, wherein the shaft comprises a knob configured to be grasped by the fingers of a practitioner;
   wherein the plunger comprises plunger threads configured to be selectively engaged and disengaged with the coupling member threads, wherein the plunger threads are configured to be retractable from the coupling member threads.

2. The inflation device assembly of claim 1, wherein the knob is rotatably coupled to the shaft.

3. The inflation device assembly of claim 1, wherein the knob comprises grip enhancing features.

4. The inflation device assembly of claim 1, wherein the shaft is releasably coupled to the handle.

5. The inflation device assembly of claim 4, wherein a portion of the shaft is disposed within the handle of the inflation device.

6. The inflation device assembly of claim 4, wherein a portion of the shaft comprises a compliant material.

7. The inflation device assembly of claim 4, wherein a portion of the crank member fits over a portion of the handle.

8. An inflation device assembly, comprising:
   a syringe body;
   a plunger configured for advancement and retraction within the syringe body; and
   a coupling member comprising coupling member threads configured to constrain movement of the plunger within the syringe body;
   a handle fixedly coupled to a proximal portion of the plunger such that the handle is configured to rotationally and axially displace the plunger, the handle comprising an elongate portion coupled to the plunger, the elongate portion extending in a direction perpendicular to a longitudinal axis of the plunger; and
   a crank member coupled to the elongate portion of the handle, wherein the crank member comprises a clip member configured to couple the crank member to the handle;
   wherein the plunger comprises plunger threads configured to be selectively engaged and disengaged with the coupling member threads, wherein the plunger threads are configured to be retractable from the coupling member threads.

* * * * *